United States Patent [19]

Liu et al.

[11] 4,368,265
[45] Jan. 11, 1983

[54] CULTURING A STRAIN OF NOCARDIA TO PRODUCE ANTIBIOTIC X-14868A

[75] Inventors: Chao-Min Liu, Cedar Grove; Barbara Prosser, Bloomfield; John Westley, Cedar Grove, all of N.J.

[73] Assignee: Hoffmann-La Roche Inc., Nutley, N.J.

[21] Appl. No.: 237,544

[22] Filed: Feb. 23, 1981

Related U.S. Application Data

[62] Division of Ser. No. 116,696, Jan. 30, 1980, Pat. No. 4,278,663.

[51] Int. Cl.³ .................. C12P 19/60; C12P 17/18
[52] U.S. Cl. .................................. 435/75; 435/119
[58] Field of Search ................................ 435/75, 119

[56] References Cited

U.S. PATENT DOCUMENTS 4,162,940  7/1979  Higashide et al. ................ 435/119
4,189,537  2/1980  Martin et al. ...................... 435/75

OTHER PUBLICATIONS

Biosynthesis, Antibiotics vol. IV, edited by Corcoran, Published by Springer-Verlag N.Y. pp. 43 & 44 (1981).

*Primary Examiner*—Alvin E. Tanenholtz
*Attorney, Agent, or Firm*—Jon S. Saxe; Bernard S. Leon; Frank P. Hoffman

[57] ABSTRACT

Antibiotic X-14868A having the following chemical structure

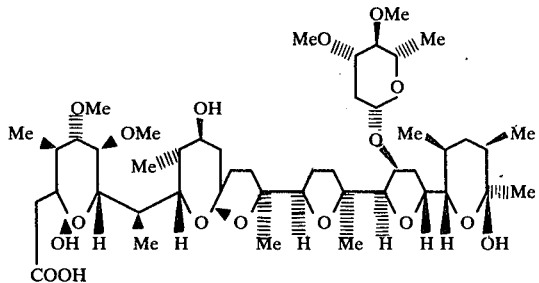

and the pharmaceutically acceptable salts thereof is presented.

Also presented is a fermentative method of producing the above antibiotic.

Antibiotic X-14868A exhibits anticoccidiostatic activity.

1 Claim, 4 Drawing Figures

CULTURING A STRAIN OF NOCARDIA TO PRODUCE ANTIBIOTIC X-14868A

This is a division of application Ser. No. 116,696, filed Jan. 30, 1980, now U.S. Pat. No. 4,278,663.

DESCRIPTION OF THE INVENTION

The present invention relates to the novel antibiotic X-14868A which has the formula and the pharmaceutically acceptable salts thereof.

As utilized in the structural formulas herein the expression Me stands for the term methyl.

There is further provided according to the present invention a fermentation process for the production of such antibiotic substance together with the isolation techniques utilized to recover the antibiotic compound from the fermentation broth.

The organism producing the antibiotic of the present invention is a new species designated Nocardia sp. X-14868. A culture of the living organism, given the laboratory designation X-14868, has been deposited in the American Type Culture Collection, Rockville, Md. and added to its permanent collection of microorganisms as ATCC 31585. The culture has been identified as a strain of Nocardia.

The new microorganism was isolated from a soil sample collected from beach sand in Colloroy, Australia. A representative strain of Nocardia sp. X-14868 has the following characteristics:

General Characteristics

Nocardia sp. X-14868 is characterized by its lack of aerial spore formation, fragmentation of the Gram positive substrate mycelium after several days of incubation and cell wall composition consisting of meso-diaminopimelic acid, galactose and arabinose.

Growth Characteristics

The organism was cultivated on the standard ISP media (Difco) described by Shirling and Gottlieb "Methods for Characterization of Streptomyces Species", Intern. J. System. Bacteriol., 16, pp 313–340, 1966, as well as various other media used to characterize the culture as listed below:

Yeast extract:
  yeast extract, 1.0%; glucose, 1.0%; agar, 1.5%; pH 6.8
Glucose-Yeast extract-peptone:
  glucose, 0.3%; yeast extract, 0.5%; peptone, 0.5%; $CaCO_3$, 0.75%; agar, 1.5%, pH 7.0
Glucose-asparagine:
  glucose 1.0%; asparagine, 0.05%; $K_2HPO_4$, 0.05%; agar, 1.5%; pH 6.8
Sucrose-nitrate:
  sucrose, 1.0%; $NaNO_3$, 0.2%; $K_2HPO_4$, 0.1%; $MgSO_4 7H_2O$, 0.05%; KCl, 0.05%; agar, 1.5%.

Media utilized in other tests were those from the following references:

| | References | |
|---|---|---|
| A. | Sodium Chloride tolerance | Gordon and Smith, "Rapidly Growing Acid Fast Bacteria", J. Bacteriol., 66:41–48, 1953 |
| B. | Hydrolysis of casein | |
| C. | Reduction of nitrate | |
| D. | Gelatin (modified with Actinomyces broth [Difco] plus 2.0% agar in meat infusion agar) | Skerman, "A Guide to the Identification of the Genera of Bacteria", William and Williams Co., Baltimore, 1967. |
| E. | Starch (Actinomyces broth [Difco] plus 0.25% soluble starch and 2.0% agar) | |
| F. | Action on Litmus Milk (Difco) | |
| G. | Resistance to Lysozyme | Gordon, "Some Criteria for the Recognition of Nocardia..", J. Gen. Microbiol., 45:355–364, 1966. |
| H. | Sensitivity to penicillin (10 unit discs) | |

Test were run at 28° and 37° C. for almost all media. Color determinations were made after 2 and 4 weeks of incubation.

Carbon utilization was determined by the method of Shirling and Gottlieb (above) using ISP-9 (Difco) medium.

A 48 hour-old ISP-1 broth culture of X-14868 was centrifuged and homogenized to obtain a washed suspension for inoculation.

The ability of the organisms to grow at 10°, 28°, 36°, 45° and 50° C. was investigated by inoculating broth of ISP-1 (Difco) medium. Cell wall analysis of the isomer of diaminopimelic acid was performed by the method of Becker et al., Appl. Microbiol., 12, 421–423, 1964. For sugar content of the cell wall, the method of Lechevalier and Lechevalier, Actinomycetales, Ed. H. Prauser, Gustav Fischer, Jena, p 311–316, 1970 was followed. Nocardomycolic acid analysis was performed by a slight modification of the method of Lechevalier, Lechevalier, and Horan, Can. J. Microbiol. 19:965–972, 1973.

Results

Microscopic Examination

Strain X-14868 produces a substrate mycelium, which fragments after several days allowing extensive mycelial development. It produces an aerial mycelium consisting of rope-like tufts but no spores were found.

Cell Wall Analysis

The cell wall contains the meso-isomer of diaminopimelic acid as well as galactose and arabinose (cell wall type IV of the classification by Lechevalier et al., Adv. Appl. Microbiol., 14, 47–72, 1971). The organism appears to produce nocardomycolic acids. These morphological and chemical criteria assign X-14868 to the genus Nocardia.

Microscopic Examination

Table 1 summarizes the amount of growth, degree of sporulation, aerial mass color, color of reverse substrate mycelium and presence of any soluble pigment produced by Strain X-14868 on various solid media after 4 weeks of incubation at 28° C.

In Table 3 is a list of diagnostically important, mostly metabolic, properties.

TABLE 3

| Characteristics of X-14868 | |
|---|---|
| Test | Result |
| ISP 1, darkening | — |
| ISP 6, darkening | — |
| ISP 7, melanin | — |
| Casein hydrolysis | + + |
| Gelatin hydrolysis | + + |
| Starch hydrolysis | — |
| NaCl (%) tolerance | 5% |
| Temperature at which growth was observed | 28 and 36° C. |

TABLE 1

| Cultural Characteristic of Strain X-14868 | | | |
|---|---|---|---|
| Agar Medium | Amount of Growth and Aerial Mycelium | Color of Aerial Mycelium[a] | Color of Reverse Substrate Mycelium[a] |
| Yeast malt extract (ISP-2) | moderate to abundant growth; some aerial mycelium in isolated edges, leathery growth | b (oyster white) | 2 ie (lt. mustard tan) |
| Oatmeal (ISP-3) | moderate growth; moderate aerial mycelium | b (oyster white) | 3 dc (natural) |
| Inorganic Salts-Starch (ISP-4) | sparse growth; sparse aerial mycelium | b (oyster white) | 2 dc (natural, string) |
| Glycerol asparagine (ISP-5) | poor growth; nearly no aerial mycelium; substrate mycelium | b (oyster white) | 2 ge (covert tan) |
| Yeast extract | abundant growth; sparse aerial mycelium; leathery | b (oyster white) | 3 ge (beige) |
| Glucose-Yeast extract-peptone | moderate growth; sparse aerial mycelium at edge; leathery, brown soluble pigment | b (oyster white) at edge | 3 ge (beige) |
| Glucose-asparagine | moderate growth; some aerial mycelium; leathery | 2 dc (natural, string) | 3 ge (beige) |
| Sucrose-nitrate | sparse growth; moderate aerial mycelium | b (oyster white) | translucent c (lt. gray) |

Note:
No spores were found in the aerial mycelium on any of the media examined after 4 weeks of incubation.
[a]The color scheme used was Color Harmony Manual, tth ed. 1958 (Container Corporation of America, Chicago).

Physiological Characteristics

Strain X-14868 hydrolyzed gelatin and casein but not starch. The culture was resistant to a 10 unit disk of penicillin as well as 0.005% lysozyme dissolved in broth when tested according to the method of Gordon, J. Gen. Microbiol., 45, 355–364, 1966. The strain completely peptonized litmus milk. No melanin production was detected on ISP 1, 6 or 7.

Table 2 reports the results of carbon utilization on ISP 9 (Difco) by Strain X-14868 at 28° C. after one month incubation.

TABLE 2

| Carbon Utilization by Strain X-14868 | |
|---|---|
| Carbon Source | Response[a] |
| No carbon control | — |
| D-Glucose | + + |
| D-Xylose | — |
| L-Arabinose | — |
| L-Rhamnose | — |
| D-Fructose | ± |
| D-Galactose | + |
| Raffinose | — |
| D-Mannitol | — |
| i-Inositol | — |
| Salicin | ± |
| Sucrose | — |
| Cellulose | — |

[a]—, negative response;
±doubtful response;
+more growth than on carbon control but less than on glucose;
+ +positive response, equal to the amount of growth on glucose.

| | |
|---|---|
| Reverse side pigment | none |
| Soluble pigment | brown on glucose yeast extract-peptone |
| Penicillin (10 unit disk) sensitivity | — |
| Nitrate reduction | + + |
| Gram strain | + |
| Acid fast stain | — |
| Catalase | + |
| Diaminopimelic acid | meso-isomer |
| Cell wall sugars | galactose, arabinose, ribose |
| Production of nocardomycolic acid | + |

The species Nocardia X-14868 described herein includes all strains of Nocardia which produce the antibiotic X-14868A and which cannot be definitely differentiated from the culture Nocardia X-14868 and its subcultures including mutants and variants thereof. The compound X-14868A is structurally identified herein and after this identification is known, it is easy to differentiate the strains producing the antibiotic compound X-14868A from others.

The pharmaceutically acceptable salts of antibiotic X-14868A can be prepared by conventional means. These salts are prepared from the free acid form of the antibiotic by methods well-known in the art, for example, by washing the free acid in solution with a suitable base or salt. Examples of such pharmaceutically acceptable basic substances capable of forming salts for the purpose of the present invention include alkali metal bases such as sodium hydroxide, potassium hydroxide, lithium hydroxide and the like; alkaline earth metal bases such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Nocardia X-14868, when grown under suitable conditions, produces the compound X-14868A. A fermentation broth containing Nocardia X-14868 is prepared by inoculating spores or mycelia of the organism producing the compound X-14868A into a suitable medium and then cultivating under aerobic conditions. For the production of the X-14868A, cultivation on a solid medium is possible but for production in large quantities, cultivation in a liquid medium is preferable. The temperature of the cultivation may be varied over a wide range, 20°-35° C., within which the organism may grow but a temperature of 26°-30° C. and a substantially neutral pH are preferred. In the submerged aerobic fermentation of the organism for the production of the antibiotic X-14868A, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distiller's solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It may also contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of the antibiotic X-14868A.

The following table sets forth the antimicrobial activity of antibiotic X-14868A and the three minor components X-14868B; X-14868C; and X-14868D.

TABLE 4

| Microorganism | Minimum Inhibitory Concentration (mcg/ml) of Antibiotics | | | |
|---|---|---|---|---|
| | X-14868A | X-14868B | X-14868C | X-14868D |
| G (+) cocci | | | | |
| Streptococcus faecium ATCC 8043 | 0.313 | 1.57 | 0.79 | 0.19 |
| Staphylococcus aureus 82 ATCC 6538p | 6.25 | 6.25 | 62.5 | 12.5 |
| Sarcina lutea PCI ATCC 9341 | 12.5 | 12.5 | 250 | 62.5 |
| G (+) rods | | | | |
| Bacillus megaterium 164 ATCC 8011 | 12.5 | 7.5 | 125 | 61.5 |
| Bacillus sp. E ATCC 27859 | 0.39 | 0.79 | 6.25 | 1.57 |
| Bacillus subtilis NRRL 558 | 12.5 | 25 | 250 | 62.5 |
| Bacillus sp. TA ATCC 27860 | 6.25 | 12.5 | 125 | 25 |
| G (+) filaments | | | | |
| Mycobacterium phlei 78 ATCC 355 | 12.5 | 25 | 250 | 62.5 |
| Streptomyces cellulosae 097 ATCC 3313 | 25 | 25 | 500 | 125 |
| Molds | | | | |
| Paecilomyces varioti M16 ATCC 26820 | 250 | 500 | * | * |
| Penicillium digitatum 0184 ATCC 26821 | 1000 | 1000 | * | * |
| Yeast | | | | |
| Candida albicans 155 NRRL 477 | 250 | 100 | * | * |
| Saccharomyces cerevisiae 90 NRRL 4226 | 1000 | * | * | * |

*Inactive at 1 mg/ml against molds and yeasts tested.

As indicated in Table 4, antibiotic X-14868A and its three minor components possess the property of adversely affecting the growth of certain gram-positive bacteria. They would therefore be useful in wash solutions for sanitary purposes as in the washing of hands and the cleaning of equipment, floors or furnishings of contaminated rooms or laboratories.

The following table sets forth the anticoccidostatic activity versus that of an infected untreated control (IUC) and an uninfected untreated control (UUC) following the test method set forth below.

TABLE 5

| Group | Conc., % | Weight gain, % | Mortality % | Average Degree of Infection Intestinal Lesion Score | | | |
|---|---|---|---|---|---|---|---|
| | | | | Upper | Mid | Ceca | Avg. |
| UUC | | 100 | 0 | 0.0 | 0.0 | 0.0 | 0.0 |
| IUC | | 37 | 20 | 2.7 | 2.0 | 3.0 | 2.6 |
| X-14868A, sodium salt Lot-1 | 0.002 | 39 | 0 | 0.0 | 0.0 | 0.0 | 0.0 |
| | 0.001 | 81 | 0 | 0.2 | 0.0 | 0.0 | 0.07 |
| | 0.0005 | 96 | 0 | 0.4 | 0.3 | 0.0 | 0.2 |
| X-14868A, sodium salt Lot-1A | 0.002 | 60 | 0 | 0.0 | 0.0 | 0.0 | 0.0 |

Test Method

This test utilizes ten chickens per drug group. Ten chickens are employed as a weight control and ten chickens as an infected control. The drug is given 48 hours in advance of the infection. One gm of the test drug is mixed in a mechanical mixer with a sufficient amount of chicken feed to result in the desired dosage. The infection consists of approximately 300,000 oocysts given orally by pipette of Eimeria acervulina, E. mivati, E. maxima, E. necatrix and E. tenella. The test lasts for six days and then the surviving birds are autopsied and examined for gross lesions in the ceca. The test birds are rated according to the number of survivors and the number of intestinal lesions. The results are expressed as average degree of infection (A.D.I.). An average degree of infection of less than 2.5 is considered significant.

The coccidiostatic compositions of this invention containing as the active ingredient, antibiotic X-14868A or its pharmaceutically acceptable salts or the dried unfiltered broth are prepared by mixing the active ingredient with an inert ingredient. The inert ingredient can comprise a feedstuff, extender materials and the like. By the term "inert ingredient" is meant a material which does not function as an antiparasitic agent, e.g., a coccidiostat, is inactive with respect to the active ingredient and which may be safely ingested by the animals to be treated, and thus, such inert material is one which is inactive for the purpose of the present invention.

The active ingredient when orally administered to coccidiosis susceptible domestic animals, particularly fowl such as turkeys and chickens, as a component of feed, effectively controls the disease by either preventing it or curing it after it occurs. Furthermore, the treated fowl either maintain their weight or actually gain weight when compared to controls. Thus, the compositions of this invention not only control coccidiosis, but also aid in improving the efficiency of conversion of feed to weight gains.

The actual concentration of the active ingredient in animal feed can, of course, be adjusted to the individual needs and may vary over a wide range. The limiting criteria of the concentration are that the minimum concentration is such that a sufficient amount of active ingredient is provided to effect the desired control of coccidiosis and the maximum concentration is such that the amount of composition ingested does not result in any untoward or undesirable side effects.

Thus, for example, a feed premix or complete feed contains sufficient active ingredient to provide from about 0.0003% to about 0.001% by weight of the daily feed consumption. Preferably about 0.0005% to 0.001% by weight is used. Generally, about 0.0005% of the active ingredient is sufficient for the purpose of controlling and combating coccidiosis. Amounts greater than 0.001%, while being effective against coccidiosis, do not generally show improved results over 0.001% and in some cases may adversely affect the growth, feed efficiency and mortality.

Even though amount over 0.001% are efficacious for combatting coccidiosis, this amount is the preferred upper range because of economics, i.e., the cost per unit of effectiveness is lowest within this range. Amounts lower than 0.0003% are not effective for combating coccidiosis. Preferred is a lower limit of 0.0005% because this insures efficaciousness. The most preferred amount, i.e., about 0.0005% by weight of the poultry daily feed consumption is particularly efficacious since it achieves maximum effect with minimum dose.

The optimum dose level will, of course, vary with the size of the animal. When using the antibiotics in accordance with the invention for treating or preventing coccidiosis, it can be first compounded or blended with a feed ingredient or carrier to become a feed additive premix, a feed concentrate, or a feed additive supplement. A feed additive, concentrate or premix is an article intended to be diluted to produce a complete feed, i.e., an article intended to be administered as a sole ration. A feed additive supplement is an article intended for consumption by an animal directly or which can be further diluted to produce a complete feed or can be ingested and used as a supplement to other rations. Feed additive supplements, concentrates and premixes contain a relatively large percentage of coccidiostats, i.e., the active ingredient to a suitable carrier and mixing in a manner to give substantially uniform dispersion of the coccidiostat in the carrier. Suitable carriers are solids that are inert with respect to the active ingredient and which may safely be ingested by the animals to be treated. Typical of such carriers are commercial poultry feeds, ground cereal grains, grain by-products, plant protein concentrates (soy, peanuts, etc.) fermentation by-products, salts, limestone, inorganic compounds, and the like or admixtures thereof. Liquid dispersions can be prepared by using water or vegetable oil preferably including a surface active agent, emulsifying agent, and the like, in the liquid dispersion such as ethylenediaminetetraacetic acid, etc. and solubilizers. Any suitable carrier or extender material can function as the inert ingredient in the solid form of the antiparasitic agent provided that it is inert to the active material and is non-toxic insofar as the animal to which it is to be administered is concerned.

The active ingredient may be blended into a mash, pellet, or any desired configuration with the inert carrier or extender solid material by any convenient technique. For example, compositions can be formed by finely grinding or pulverizing the active ingredient and the inert ingredient using any commercially avaiable grinder or pulverizer with or without the feed material being present. If the feed material is not present when the grinding or pulverizing is effected, the resultant material can be distributed, in accordance with the present invention, in any conveniently available feed material. Typical poultry feeds, which can be medicated with the active ingredient of this invention can contain several ingredients, for example, they can contain high energy grain products such as corn, wheat, wheat red dog flour, milo, oatmeal, or the like; medium and low energy grain products, such as oats, barley, wheat flour, middlings, standard middlings or the like; stabilized fats; vegetable protein such as soybean meal, corn gluten meal, peanut meal, or the like; animal protein such as fish meal, fish solubles, meat scraps or the like; UGF (unidentified growth factor) sources and other B-vitamin carriers such as dried milk products, dried brewers yeast, distillers dried solubles, fermentation solubles, or the like; dehydrated alfalfa meal; and various special additives such as additional riboflavin, vitamin $B_{12}$, calcium pantothenate, niacin, choline, vitamin K and vitamin E or the like, as well as stabilized vitamin A, vitamin $D_3$ (D-activated animal sterols); calcium and phosphorus supplements such as dicalcium phosphate, steamed bone meal, defluorinated phosphate, limestone, or the like; iodized salt, manganese sulfate, zinc carbonate, an antibiotic feed supplement; methionine or its hydroxy analog, and an antioxidant.

As is evident from the above, the coccidiostat compositions are intended for oral ingestion. They can be added to the normal feed supply of the treated animal or can be administered by other procedures, such as incorporating the same in a tablet, pill or bolus and supplying it forcibly to the animal. The administration of the active ingredient must be considered in terms of the specific animal under the husbandry practices encountered.

The minor components X-14868B, C and D also exhibit anticoccidiostatic activity when tested in vitro. X-14868B also has been shown to be active in vivo.

Antibiotic X-14868A has also been found to exhibit activity as a growth promotant in ruminants, i.e., animals with a rumen function, for example, cattle. A discussion of the mechanism whereby feed is digested, degraded and metabolized in a ruminant animal can be found in U.S. Pat. No. 3,839,557 issued Oct. 1, 1974 which discloses the use of certain antibiotics in improving ruminant feed utilization and is incorporated herewith by reference. Economically important ruminant animals include cattle, sheep and goats.

The effectiveness of antibiotic X-14868A in modifying the ratio of volatile fatty acids produced in the rumen (and thereby improve ruminant feed utilization) is demonstrated by means of the in vitro testing.

Rumen fluid is obtained from a steer with a fistulated rumen. The steer is maintained on the following ration:
Corn: 89.93%
Alfalfa meal: 5.000%
Soy bean oil meal: 3.00%
Limestone: 0.80%
NaCl: 0.60%
Dicalcium phosphate: 0.50%
Trace minerals: 0.025%
Vitamin premix additions: 0.1%
  Vitamin A, TIU: 4.0003
  Vitamin $D_3$, IU: 0.801
  Vitamin E, TIU: 3.002

The rumen fluid is immediately strained through a #30 mesh sieve. For each fermentation, 75 ml of the resulting fluid is added to a 250 ml flask containing the following:
1 g of 80%:20% finely ground grain: hay ration;
1 ml of an 18% aqueous glucose solution (1 millimole per flask);
1.5 ml of a 3.1% aqueous urea solution (0.76 millimole per flask);
60 micromoles of each of the 10 essential amino acids (arginine, histidine, leucine, methionine, threonine, valine, lysine, isoleucine, phenylalanine, tryptophan);
1 ml of an aqueous solution of test drug to give either 10 or 25 μg/ml (calculated total volume of fermentation mixture of 80 ml);

Each flask is incubated at 38° C. in a shaking water bath equipped with a gassing hood. Carbon dioxide is continuously passed through the hood. After four hours incubation, a 10 ml quantity of the fermentation fluid is centrifuged at 14,000 rpm (approximately 30,000 xg) for 20 minutes in an International Centrifuge equipped with a No. 874 angle head. Three ml of the supernate is added to 1 ml of a 25% metaphosphoric acid solution containing 23 micromoles 2-methyl valeric acid as an internal standard. The resulting fluid is permitted to sit at room temperature for 30 minutes. The fluid is filtered through a 0.22 millimicron Millipore filter and refrigerated until gas-liquid chromatographic analyses for volatile fatty acids.

Gas-liquid chromatographic (GLC) analyses of four in vitro control fermentations and two fermentations each with 10 and 25 ppm antibiotic X-14868A are set forth in the following table.

TABLE 6

Ratios of moles of propionate ($C_3$) to acetate ($C_2$) plus n-butyrate ($nC_4$) in vitro rumen fermentations

| Compound | Concentration | VFA Molar Ratio $C_3/(C_2 + nC_4)$ | % Positive Control |
|---|---|---|---|
| Negative Control | 0 | 0.203 | 51.8 |
| X-14868A | 5 ppm | 0.323 | 82.5 |
|  | 50 ppm | 0.358 | 91.2 |
| Positive Control (Monensin) | 50 ppm | 0.392 | 100.0 |

As shown in Table 6 the ratio of propionate ($C_3$) to acetate and n-butyrate is significantly improved. With the increase of propionates rather than acetates from the carbohydrates, the efficiency of carbohydrate and therefor feed utilization is increased.

Administration of antibiotic X-14868A hereafter "Antibiotic" or "Antibiotic Compound" prevents and treats ketosis as well as improves feed utilization. The causative mechanism of ketosis is a deficient production of propionate compounds. A presently recommended treatment is administration of propionic acid or feeds which preferentially produce propionates. It is obvious that encouraging propionate production from ordinary feeds will reduce incidence of ketosis.

It has been found that antibiotic X-14868A increases the efficiency of feed utilization in ruminant animals when it is administered orally to the animals. The easiest way to administer the antibiotic is by mixing it in the animal's feed.

However, the antibiotic can be usefully administered in other ways. For example, it can be incorporated into tablets, drenches, boluses, or capsules, and dosed to the animals. Formulations of the antibiotic compound in such dosage forms can be accomplished by means of methods well-known in the veterinay pharmaceutical art.

Capsules are readily produced by filling gelatin capsules with any desired form of the desired antibiotics. If desired, the antibiotic can be diluted with an inert powdered diluent, such as a sugar, starch, or purified crystalline cellulose in order to increase its volume for convenience in filling capsules.

Tablets of the antibiotic are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly-used absorbents again include starch and lactose while magnesium carbonate is also useful for oily substances. Frequently-used binders are gelatin, gums, starch, dextrin and various cellulose derivatives. Among the commonly used lubricants are magnesium stearate, talc, paraffin wax, various metallic soaps and polyethylene glycol.

The administration of the antibiotic compound may be as a slow-pay-out bolus. Such boluses are made as tablets except that a means to delay the dissolution of the antibiotic is provided. Boluses are made to release for lengthy periods. The slow dissolution is assisted by choosing a highly water-insoluble form of the antibiotic. A substance such as iron filing is added to raise the density of the bolus and keep it static on the bottom of the rumen.

Dissolution of the antibiotic is delayed by use of a matrix of insoluble materials in which the drug is inbedded. For example, substances such as vegetable waxes, purified mineral waxes, and water-insoluble polymeric materials are useful.

Drenches of the antibiotic are prepared most easily by choosing a water-soluble form of the antibiotic. If an insoluble form is desired for some reason, a suspension may be made. Alternatively, a drench may be formulated as a solution in a physiologically acceptable solvent such as a polyethylene glycol.

Suspensions of insoluble forms of the antibiotic can be prepared in nonsolvents such as vegetable oils such as peanut, corn, or sesame oil, in a glycol such as propylene glycol or a polyethylene glycol; or in water, depending on the form of the antibiotic chosen.

Suitable physiologically acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants serve to suspend the antibiotic. For example, lecithin, alkylphenol polyethylene oxide adducts, naphthalenesulfonates, alkylbenzesulfonates, and the polyoxyethylene sorbitan esters are useful for making suspensions in liquid nonsolvents.

In addition many substances which effect the hydrophilicity, density, and surface tension of the liquid can assist in making suspensions in individual cases. For example, silicone anti-foams, glycols, sorbitol, and sugars can be useful suspending agents.

The suspendable antibiotic may be offered to the grower as a suspension, or as a dry mixture of the antibiotic and adjuvants to be diluted before use.

The antibiotic may also be administered in the drinking water of the ruminants. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with the antibiotic compound is by the formulation of the compound into the feed supply. Any type of feed may be medicated with the antibiotic compounds, including common dry feeds, liquid feeds and pelleted feeds.

The methods of formulating drugs into animal feeds are well-known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound, or of premix, in the feed.

All of the methods of formulating, mixing and pelleting feeds which are normally used in the ruminant feed art are entirely appropriate for manufacturing feeds containing the antibiotic compound.

As has been shown, oral administration of the antibiotic beneficially alters the production of propionates relative to the production of acetates in the rumen. It may therefore be postulated that the same treatment would also benefit monogastric animals which ferment fibrous vegetable matter in the cecum since it would be expected that a beneficial change in the propionate/acetate ration would occur upon oral administration of the instant antibiotic. Horses, swine and rabbits are exemplary animals which digest a part of their food by cecal fermentation.

Antibiotic X-14868A also has demonstrated activity as an agent in the treatment or prevention of swine dysentery. The compound was examined for activity against *Treponema hyodysenteriae*, the etiologic agent of swine dysentery. The results which represent a comparative test following well-known test methods versus a known agent in the treatment and prevention of swine dysentery are set forth in the table below.

TABLE 7

| | Minimum Inhibitory Concentration (mcg/ml) | |
|---|---|---|
| T. hyodysenterial Strain | X-14868A | Ipronidazole |
| H-78 | 0.05 | 0.63 |
| H 140 | 0.05 | 0.63 |
| B 169 | 0.05 | 0.63 |
| SQ 2 | 0.05 | 2.5 |
| Mean | 0.05 | 1.1 |

Also forming part of the present invention are the novel minor components denominated as X-14868B, C and D. These components exhibit in vitro anticoccidial activity against an *E. tenella* as set forth below.

| In vitro activity versus E. tenella | |
|---|---|
| Compound | PPM effective against E. tenella |
| X-14868B | 0.1 |
| X-14868C | 10.0 |
| X-14868D | 10.0 |

The structural formula of compound X-14868B is as follows:

The infrared absorption spectra for the respective compounds are as follows:

| X-14868A | FIG. 1 |
|---|---|
| X-14868B | FIG. 2 |
| X-14868C | FIG. 3 |
| X-14868D | FIG. 4 |

Figure 1:
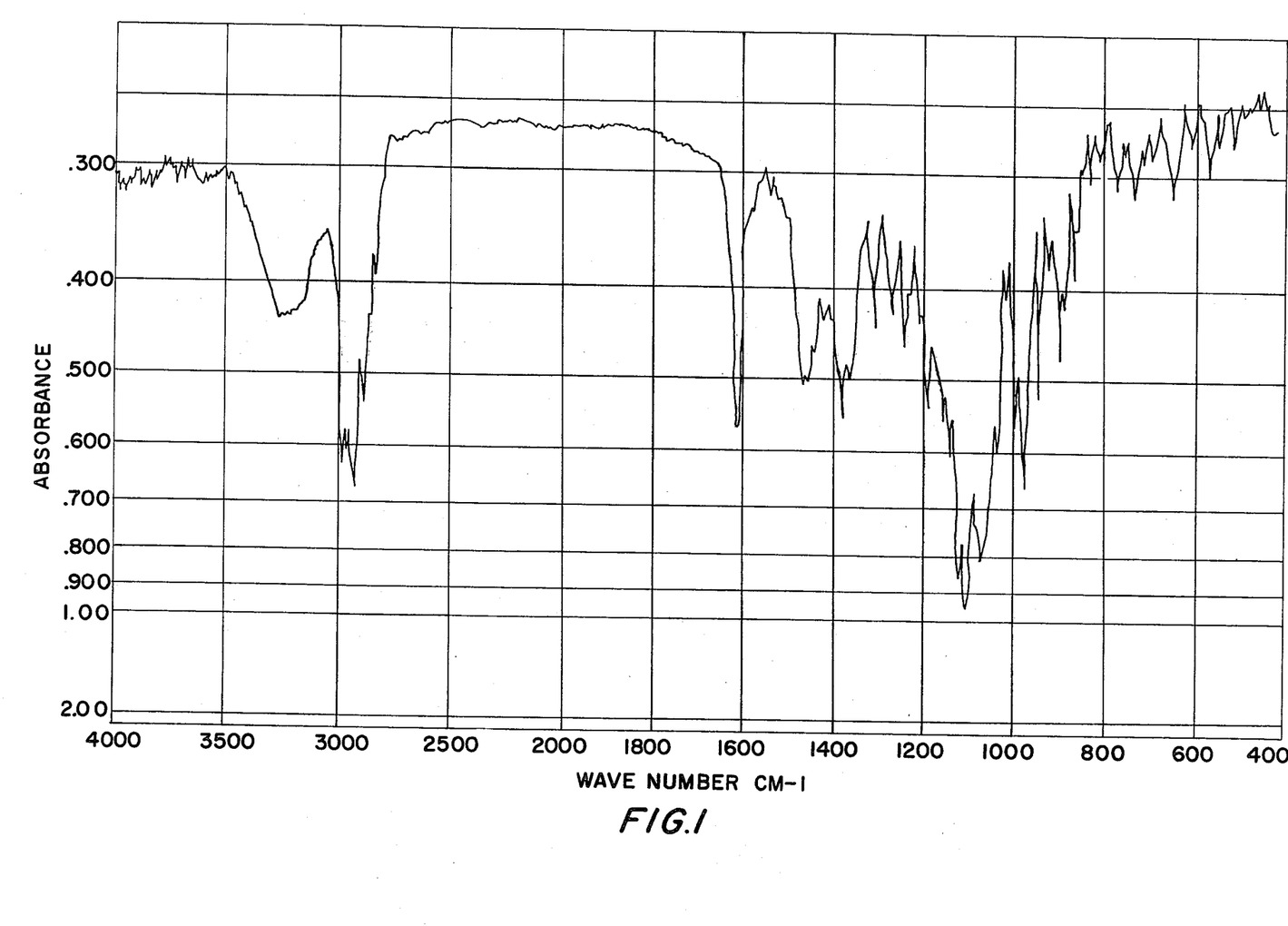
Figure 2:
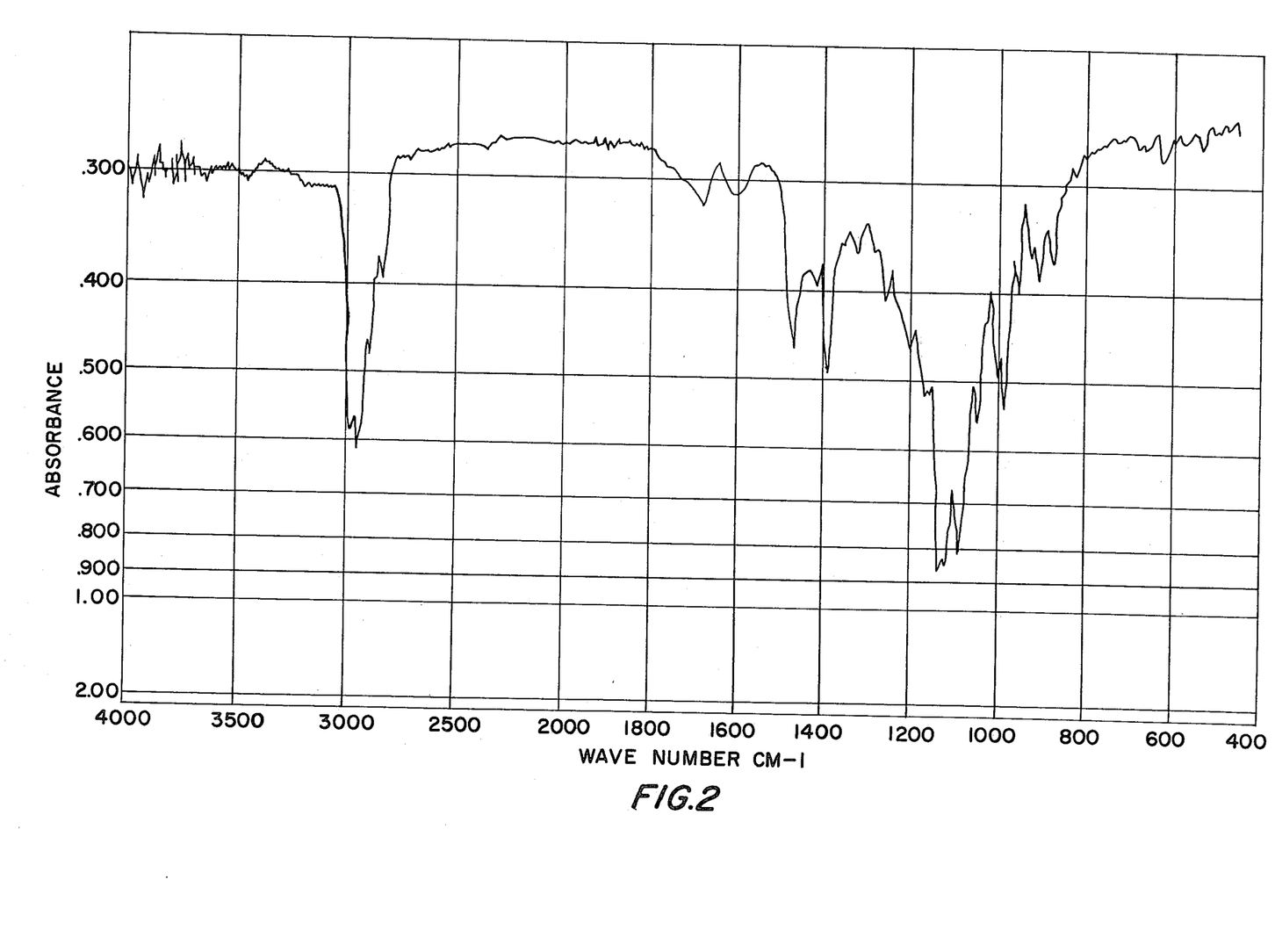
Figure 3:
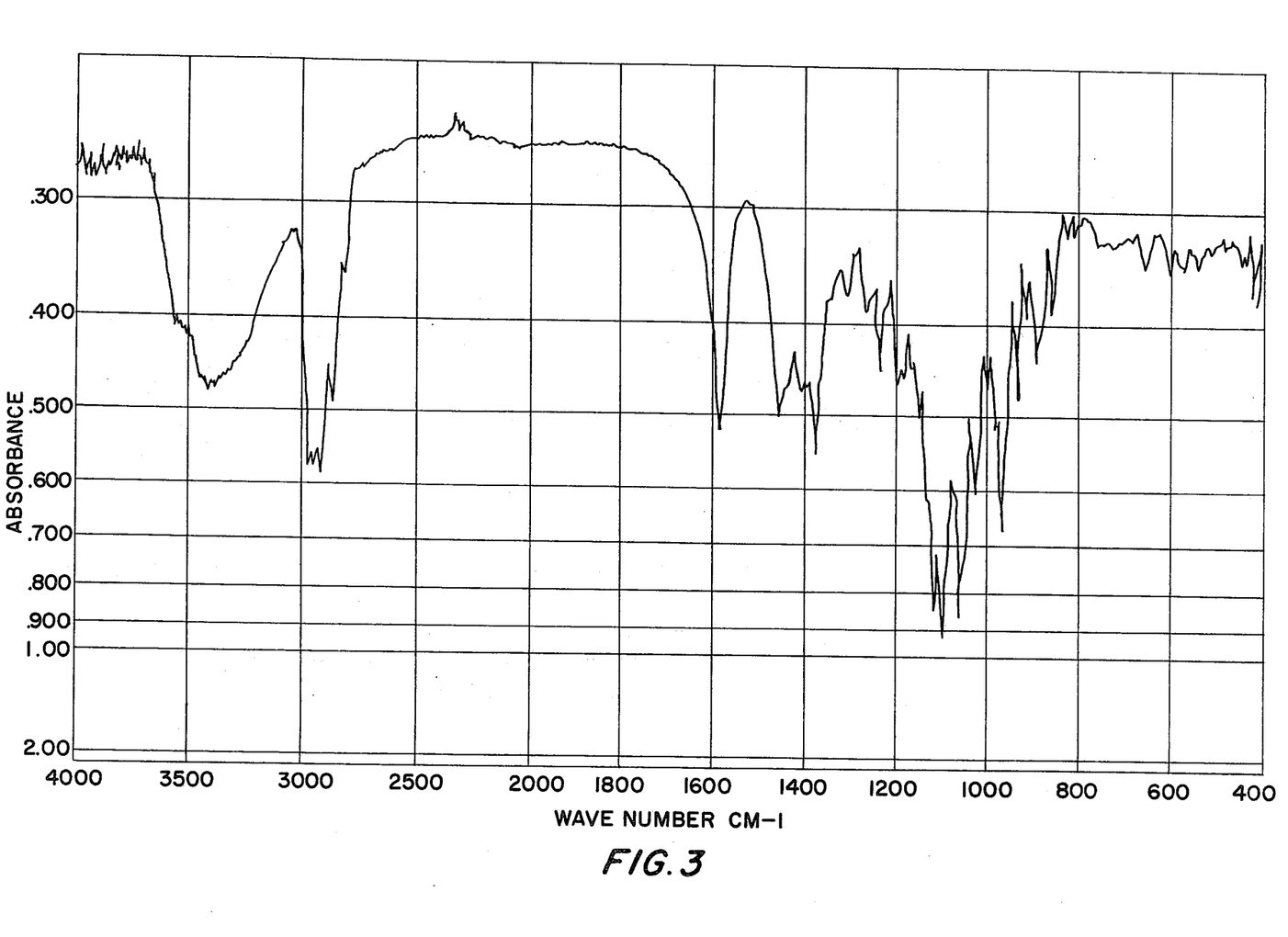
Figure 4:
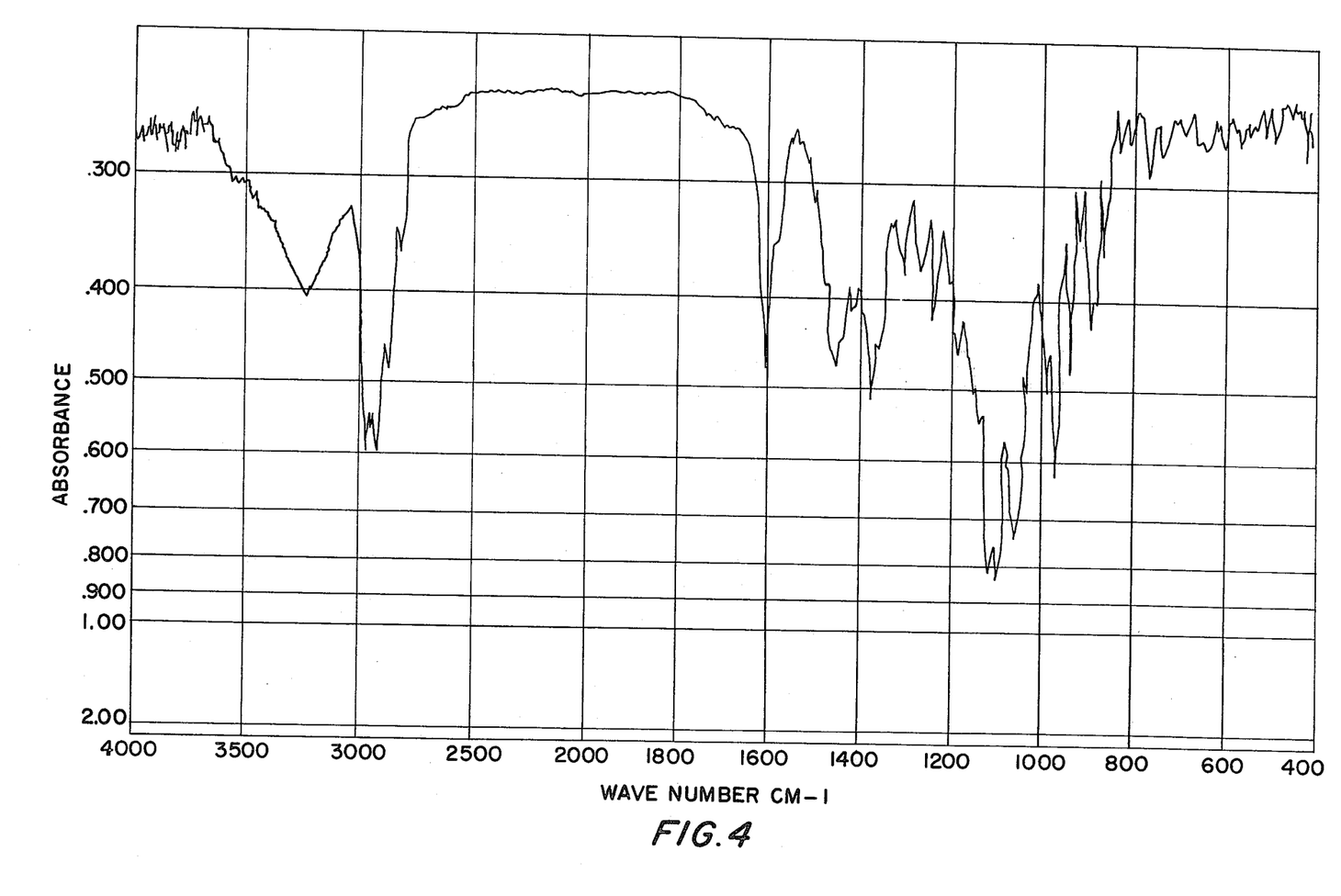

Table 8 sets forth physical constants for the various components produced by fermentation of the Nocardia X-14868.

TABLE 8

| | Physical constants of X-14868 components | | | | | | |
|---|---|---|---|---|---|---|---|
| | | [α]D, Specific rotation | | *Microanalysis found | | | |
| Component Number | M.P. °C. | chloroform | methanol | % C | % H | % Na | % OMe |
| X-14868A | 193–195 | +40.6° | +23.8° | 60.11 | 8.54 | 2.38 | 12.10 |
| X-14868B | 172.5–174 | +46.1° | +34.8° | 60.97 | 8.60 | 1.23 | 14.87 |
| X-14868C | 172–175 | +49.6° | +30.5° | 57.13 | 8.58 | 2.36 | 10.25 |
| X-14868D | 194–195 | +41.1° | +29.2° | 60.32 | 8.80 | 3.40 | |

| *Calculated Microanalysis for compounds A and B | M.W. | % C | % H | % Na | % OMe |
|---|---|---|---|---|---|
| X-14868A: $C_{47}H_{79}O_{17}Na$ | 939.25 | 60.10 | 8.50 | 2.45 | 13.22 |
| X-14868B: $C_{96}H_{163}O_{34}Na.H_2O$ | 1902.36 | 60.61 | 8.75 | 1.21 | 16.54 |

The following examples will serve to illustrate this invention without limiting it thereto.

EXAMPLE 1

Shake Flask Fermentation of Nocardia X-14868

The antibiotic X-14868A producing culture is grown and maintained on a starch-casein agar slant having the following composition (grams/liter distilled water):

| Soluble starch | 10.0 |
|---|---|
| Casein | 1.0 |
| $K_2HPO_4$ | 0.5 |
| $MgSO_4$ (anhydrous) | 0.5 |
| Agar | 20.0 |

Adjust pH to 7.4 with NaOH before autoclaving at 15 pound pressure for 20 minutes.

The slant is inoculated with Nocardia X-14868 culture and incubated at 28° C. for 7–14 days. A chunk of agar containing mycelia from the well-grown agar slant is then used to inoculate a 500-ml Erlenmeyer flask containing 100 ml sterilized inoculum medium having the following composition (grams/liter distilled water):

| Tomato pomace | 5.0 |
|---|---|
| Distillers soluble | 5.0 |
| OM peptone | 5.0 |
| Debittered dried yeast | 5.0 |
| Cornstarch | 20.0 |
| $CaCO_3$ | 1.0 |
| $K_2HPO_4$ | 1.0 |

Adjust pH to 7.0 with NaOH before sterilization.

The inoculated inoculum medium is incubated at 28° C. for 72 hours on a rotary shaker, operating at 250 rpm with a 2-inch stroke.

A 3 ml portion (3%, v/v) of the resulting culture is then used to inoculate a 500-ml Erlenmeyer flask containing 100 ml sterilized production medium having the following composition (grams/liter distilled water):

| Glycerol | 40.0 |
|---|---|
| OM peptone | 5.0 |
| Cerelose | 2.0 |
| Potato starch | 2.0 |
| Defatted soy grit (Archer Daniels Midland Co.) | 5.0 |
| Debittered dried yeast | 5.0 |
| NaCl | 5.0 |
| $CaCO_3$ | 0.2 |

Adjust pH to 6.4 before autoclaving.

The inoculated medium is incubated at 28° C. for 5 days on a rotary shaker running at 250 rpm with a 2-inch stroke. The potency of the antibiotic X-14868A in the fermentation broth is estimated by assaying against Staphylococcus aureus ATCC 6538P using agar diffusion cup-plate assay.

EXAMPLE 2

Isolation of Antibiotic X-14868A-Na Salt and Antibiotic X-14868B-Na Salt from Shake Flask Fermentation Step A:

The whole broth from 50 half-liter Erlenmeyer flasks each containing 100 ml, after 5 days of fermentation were pooled (5 liters) and extracted twice with one-half volume of ethyl acetate. After stirring for one-half hour solvent layer was separated and concentrated to an oil (4 g) under reduced pressure. The oil was dissolved in diethyl ether and was chromatographed on a diethyl ether slurry packed 200 g silica gel (Davison grade 62) column. The column was eluted with a gradient between 2 liters of diethyl ether to 2 liters diethyl ether-/acetone (9:1) and then 2 liters of diethyl ether/acetone (1:1) and then 2 liters of methylene chloride/ethyl alcohol (7:3). Fractions of 40 ml each were collected and from fraction numbers 18–75 were pooled, solvent was removed under reduced pressure and the (1.66 g) residue thus obtained was dissolved in ethyl acetate and was washed with equal volume of 1 N HCl two times, followed by washing with equal volume of $Na_2CO_3$ (saturated at room temperature) two times. The solvent phase was dried over $Na_2SO_4$, and by addition of n-hexane antibiotic X-14868A-Na salt crystals were obtained. Recrystallization from ethyl acetate/n-hexane yielded the analytical sample of antibiotic X-14868A-Na salt. M.P. 193°–194° C.

Step B:

From fraction numbers 161–215 subsequent to the solvent being removed under reduced pressure, and the residue being dissolved in ethyl acetate and washed with 1 N HCl, followed by $Na_2CO_3$ (saturated at room temperature) washing and drying over $Na_2SO_4$, after addition of n-hexane antibiotic X-14868B-Na salt crystals were obtained. M.P. 172.5°–174° C.

EXAMPLE 3

Tank Fermentation of Nocardia X-14868

The antibiotic X-14868A producing culture Nocardia X-14868 is grown and maintained on a starch-casein agar slant having the following composition (grams/liter distilled water):

| Soluble starch | 10.0 |
|---|---|
| Casein | 1.0 |
| $K_2HPO_4$ | 0.5 |
| $MgSO_4$ (anhydrous) | 0.5 |

-continued

| | |
|---|---|
| Agar | 20.0 |

Adjust pH to 7.4 with NaOH before autoclaving.

The slant is inoculated with Nocardia X-14868 culture and incubated at 28° C. for 7-14 days. A chunk of agar containing mycelia from the well-grown agar slant is then used to prepare vegetative inoculum by inoculating a 500-ml Erlenmeyer flask containing 100 ml of inoculum medium with the following composition (grams/liter distilled water):

| | |
|---|---|
| Tomato pomace | 5.0 |
| Distillers soluble | 5.0 |
| OM peptone | 5.0 |
| Debittered dried yeast | 5.0 |
| Cornstarch | 20.0 |
| $CaCO_3$ | 1.0 |
| $K_2HPO_4$ | 1.0 | pH is adjusted to 7.0 before autoclaving.

The inoculated medium is incubated for 72 hours at 28° C. on a rotary shaker operating at 250 rpm with a 2-inch stroke.

Sixty ml (3%v v/v) of this culture broth are used to inoculate a 6-liter Erlenmeyer flask containing 2-liters of inoculum medium having the following composition (grams/liter distilled water):

| | |
|---|---|
| Tomato pomace | 5.0 |
| Distillers soluble | 5.0 |
| OM peptone | 5.0 |
| Debittered dried yeast | 5.0 |
| Cornstarch | 20.0 |
| $CaCO_3$ | 1.0 |
| $K_2HPO_4$ | 1.0 | pH is adjusted to 7.0 before autoclaving.

The inoculated medium is incubated for 72 hours at 28° C. on a rotary shaker operating at 250 rpm.

Four liters of this culture are used to inoculate 60 gallons of the following production medium in a 100-gallon fermentor (grams/liter tap water):

| | |
|---|---|
| Glycerol | 40.0 |
| OM peptone | 5.0 |
| Cerelose | 2.0 |
| Potato starch | 2.0 |
| Defatted soy grit (Toasted Nutrisoy grit, 40-80) | 5.0 |
| Debittered dried yeast | 5.0 |
| NaCl | 5.0 |
| $CaCO_3$ | 0.2 |
| Sag 4130 antifoam (Union Carbide) | 0.1 |

The pH of the medium is adjusted to 6.4 before sterilization for 1¼ hours with 60 lb/in² steam.

The inoculated medium is aerated with compressed air at a rate of 3 cubic feet per minute, and is stirred with agitators at 280 rpm. The fermentation is carried out at 28° C. for 5 days.

The potency of antibiotic X-14868A in the fermentation broth is estimated by assaying against *Staphylococcus aureus* ATCC 6538P using agar diffusion cup-plate assay.

EXAMPLE 4

Isolation of Antibiotic X-14868-A-; -C; and -D Sodium Salts from Tank Fermentation of Nocardia X-14868

Step A:

To the whole broth from a sixty gallon (227.1 liters) fermentation as set forth in Example 3 was added, after 115 hours growth, an equal volume of ethyl acetate. After stirring for one hour the solvent layer was separated and concentrated to 4.2 liters under reduced pressure. The concentrated solvent extract was washed with equal volume of 1 N HCl two times, followed by washing two times with equal volume of $Na_2CO_3$ (saturated at room temperature). The solvent phase was dried over $Na_2SO_4$ and concentrated to an oil under reduced pressure. The oil was dissolved in n-hexane and was extracted once with acetonitrile followed by two extractions with acetonitrile/methanol (8:2). The acetonitrile and acetonitrile/methanol (8:2) extracts were pooled, and the solvent was removed under reduced pressure. The resulting oil was dissolved in diethyl ether, treated with charcoal (MCB, activated "Norit A"), filtered and by addition of n-hexane crude antibiotic X-14868A-Na salt crystals were obtained. The crude antibiotic crystals were dissolved in methylene chloride and were subjected to chromatography on a methylene chloride slurry packed 600 g silica gel (Davison grade 62) column. The column was eluted with 4 liters of diethyl ether/acetone/ammonium hydroxide (8/2/0.02). Fractions of 45 ml each were collected and from fraction numbers 13-15 were pooled. The solvent was removed under reduced pressure, the residue was dissolved in ethyl acetate and consecutively washed twice with 1 N HCl and twice with $Na_2CO_3$ (saturated at room temperature) dried over $Na_2SO_4$. The ethyl acetate phase was concentrated to an oil and was dissolved in methylene chloride and by addition of n-hexane crystalline antibiotic X-14868A-Na salt was obtained. M.P. 193°-195° C.

Step B:

The mother liquor of the crude antibiotic X-14868A-Na salt crystals (described in above Step A) was chromatographed on a methylene chloride slurry packed 1 kg silica gel (Davison grade 62) column. The column was eluted with 1 liter of n-hexane and then a gradient between 4 liters of diethyl ether/n-hexane (7:3) to 4 liters of diethyl ether/acetone (8:2). Fractions of 40 ml each were collected and fraction numbers 43-80 were pooled. The solvent was removed under reduced pressure and the residue was dissolved in ethyl acetate and washed with 1 N HCl, followed by the aqueous $Na_2CO_3$ (saturated at room temperature) wash and charcoal treatment (MCB activated "Norit A"). After filtration, the ethyl acetate phase was concentrated to an oil. The oil was dissolved in diethyl ether and the addition of n-hexane yielded additional antibiotic X-14868A-Na salt. M.P. 193°-195° C.

Step C:

Fraction numbers 22-40 from the silica gel column described above in Step A yielded crystalline antibiotic X-14868C-Na salt. M.P. 172°-175° C.

Step D:

The mother liquor of the crystalline X-14868A-Na salt described in Step B and fractions 16-21 from the silica gel column, described in Step A were pooled, concentrated and subjected to chromatography on a methylene chloride slurry packed 600 g silica gel column. The column was eluted with 4 liters of diethyl ether/hexane (1:1); 4 liters of diethyl ether/acetone/n-hexane/ammonium hydroxide (6:2:2:0.002); 2 liters of diethyl ether/acetone (8:2). Fractions of 40 ml each were collected. Fraction numbers 71-98 were pooled and crystallization yielded additional crystalline X-14868A-Na salt. Fraction numbers 141-172 were also pooled, solvent was removed under reduced pressure and crystallization from diethyl ether/n-hexane yielded antibiotic X-14868D-Na salt. M.P. 194°-195° C.

EXAMPLE 5

Preparation of the thallium salt of antibiotic X-14868A

A solution of 51 mg of antibiotic X-14868A-Na salt in methylene chloride was washed with 1 N HCl, followed by water wash and then four times with an aqueous solution of thallium carbonate. The solvent was separated and concentrated to a small volume under reduced pressure and after the addition of n-hexane crystalline thallium salt of antibiotic X-14868A was recovered. Recrystallization from diethyl ether/n-hexane yielded crystals suitable for X-ray analysis.

EXAMPLE 6

Preparation of the calcium salt of antibiotic X-14868A

A solution of 200 mg of antibiotic X-14868A-Na salt in ethyl acetate was first washed with 1 N HCl, then three times with an aqueous solution of calcium hydroxide (saturated at room temperature). The solvent was separated and removed under reduced pressure. The calcium salt of antibiotic X-14868A was recovered as a white solid foam.

EXAMPLE 7

Shake Flask Fermentation of X-14868

The antibiotic X-14868A producing culture was grown and maintained on a starch casein agar slant having the following composition (grams/liter distilled water):

| | |
|---|---|
| Soluble starch | 10.0 |
| Casein | 1.0 |
| $K_2HPO_4$ | 0.5 |
| $MgSO_4$ (anhydrous) | 0.5 |
| Agar | 20.0 |

Adjust pH to 7.4 with NaOH before autoclaving at 15 pound pressure for 20 minutes.

The slant was inoculated with Nocardia X-14868 culture and incubated at 28° C. for 7-14 days. A chunk of agar containing mycelia from the well-grown agar slant was then used to inoculate a 500-ml Erlenmeyer flask containing 100 ml sterilized inoculum medium having the following composition (grams/liter distilled water):

| | |
|---|---|
| Tomato pomace | 5.0 |
| Distillers soluble | 5.0 |
| OM peptone | 5.0 |
| Debittered dried yeast | 5.0 |
| Cornstarch | 20.0 |
| $CaCO_3$ | 1.0 |
| $K_2HPO_4$ | 1.0 |

Adjust pH to 7.0 with NaOH before sterilization.

The inoculated inoculum medium was incubated at 28° C. for 72 hours on a rotary shaker, operating at 250 rpm with a 2-inch stroke.

A 3 ml portion (3%, v/v) of the resulting culture is then used to inoculate a 500-ml Erlenmeyer flask containing 100 ml sterilized production medium having the following composition (grams/liter distilled water):

| | |
|---|---|
| Cerelose (C.P.C. International Co.) | 45.0 |
| Eclipse N Starch (A. E. Staley Co.) | 20.0 |
| Soyalose 105 (Central Soya Co.) | 15.0 |
| Casein hydrolysate (acid) (General Biochemicals) | 1.0 |
| Black strap molasses | 3.0 |
| $CaCO_3$ | 2.5 |
| Tap water to 1 liter | |
| pH 7.1 | |

The inoculated medium is incubated at 28° C. for 7 days on a rotary shaker running at 250 rpm with a 2-inch stroke. The potency of antibiotic X-14868A in the fermentation broth was estimated by assaying against *Staphylococcus aureus* ATCC 6538P using agar difussion cup-plate assay.

What is claimed:

1. A process to produce a compound of the formula which comprises cultivating a strain of Nocardia X-14868 in an aqueous carbohydrate solution containing a nitrogenous nutrient under submerged aerobic conditions and thereafter isolating antibiotic X-14868A from said solution.

* * * * *